Figure 1:
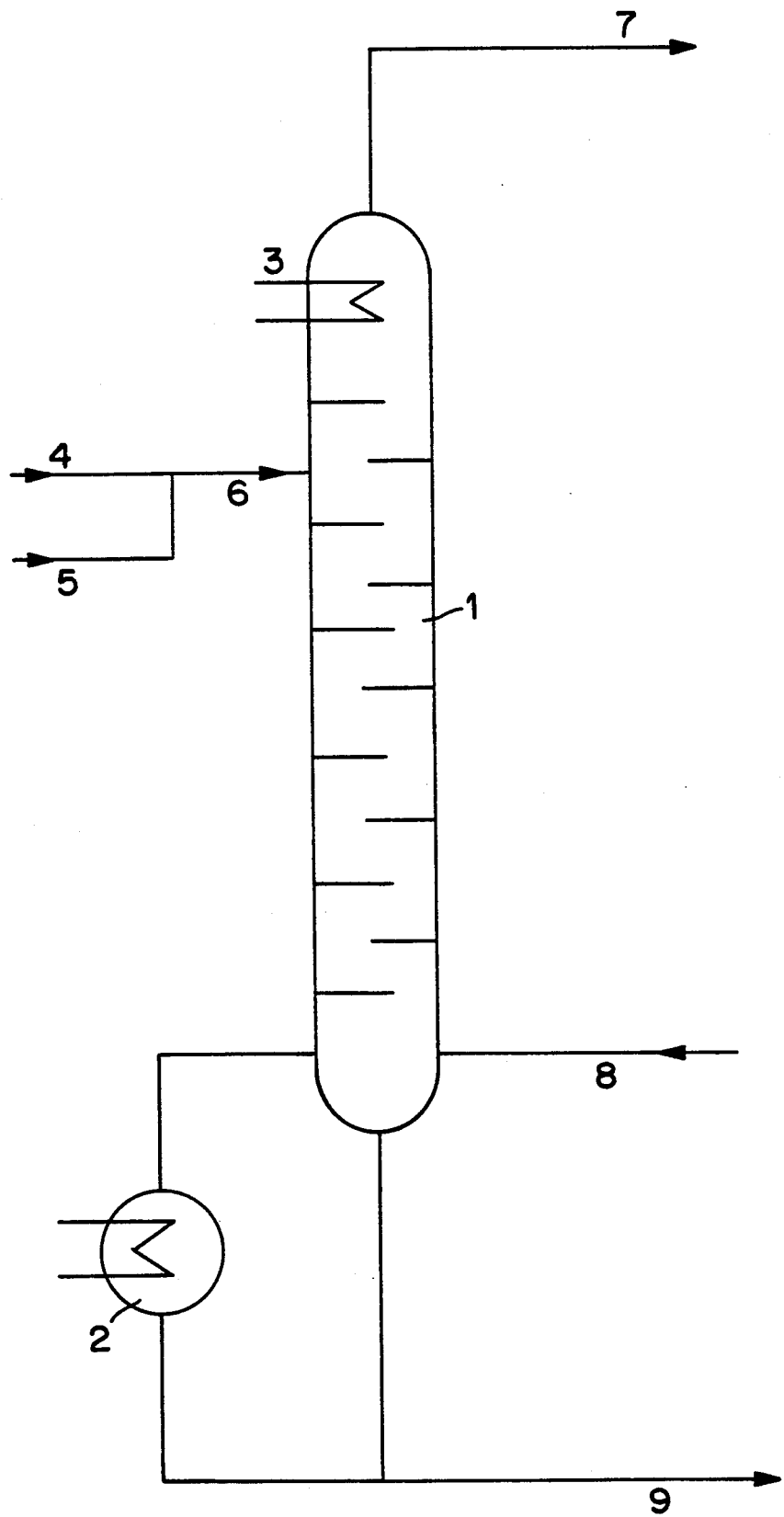

United States Patent [19]

Farnleitner et al.

[11] Patent Number: 5,189,215
[45] Date of Patent: Feb. 23, 1993

[54] PROCESS FOR THE PREPARATION OF STORAGE-STABLE LEVULINIC ACID

[75] Inventors: Lorenz Farnleitner; Hubert Stückler; Herbert Kaiser, all of Linz; Engelbert Kloimstein, Eferding, all of Austria

[73] Assignee: Chemie Linz Gesellschaft m.b.H., Linz, Austria

[21] Appl. No.: 784,746

[22] Filed: Oct. 28, 1991

Related U.S. Application Data

[63] Continuation of Ser. No. 530,967, May 25, 1990, abandoned.

[30] Foreign Application Priority Data

Jun. 5, 1989 [AT] Austria ................... 1356/89

[51] Int. Cl.⁵ ................ C07C 59/147; C07C 59/185; C07C 59/325; C07C 59/347
[52] U.S. Cl. .................................... 562/577
[58] Field of Search ......................... 562/577

[56] References Cited

U.S. PATENT DOCUMENTS 4,236,021 11/1980 Hsu et al. .................. 562/577

FOREIGN PATENT DOCUMENTS 0028234 11/1980 World Int. Prop. O. .

OTHER PUBLICATIONS

Wiggins, "Research", 3 140-145 (1950).

*Primary Examiner*—Paul J. Killos
*Assistant Examiner*—Joseph M. Conrad
*Attorney, Agent, or Firm*—Wenderoth, Lind & Ponack

[57] ABSTRACT

A process for the preparation of color-stable levulinic acid by saponification of acetylsuccinates with aqueous mineral acids, by continuously treating the starting products with steam in counter-current in a reactor cascade, the reaction being carried out above the boiling point of the alcohol being formed in the reaction or above the boiling point of the aqueous azeotrope being formed.

11 Claims, 1 Drawing Sheet

PROCESS FOR THE PREPARATION OF STORAGE-STABLE LEVULINIC ACID

This application is a continuation of now abandoned application Ser. No. 07/530,967 filed on May 25, 1990 now abandoned.

The invention relates to a process for the preparation of storage-stable levulinic acid by saponification of acetylsuccinates.

Levulinic acid is a starting product for the preparation of organic chemicals, dyestuffs, polymers, pharmaceutically active compounds and flavor substances. Particularly in the use of levulinic acid for the preparation of polymers, pharmaceutically active compounds and flavour substances, stringent requirements regarding purity, color and stability of the levulinic acid are laid down.

Several processes for the preparation of levulinic acid, on the basis of different starting compounds, are already known.

The preparation of levulinic acid from carbohydrates by the action of mineral acids is known from G. J. Mulder, J. prakt. Chem. 21, 219 (1840), cited in L. F. Wiggins, Research 3, (1950), 140. In addition to formic acid, further by-products, of which some are insoluble and some are deeply colored and which cannot be completely separated off, are formed in yields of 40-60%. Levulinic acid prepared in this way already shows a marked brown to reddish-tinged coloration and rapidly darkens further on storage, that is to say it is not colour-stable.

DEA 2,112,726 has disclosed the preparation of levulinic acid starting from furfuryl alcohol by ring cleavage with hydrochloric acid or oxalic acid. To improve the yield, this process is carried out in a very dilute solution, which entails a high energy consumption in separating off the solvent. Levulinic acid prepared in this way, however, shows very rapid dark discoloration even under a brief thermal stress, that is to say it has a low colour stability.

EP-A 0,028,234 has disclosed a process for the preparation of levulinic acid, wherein furfuryl alcohol is first esterified in the presence of an acid catalyst to give a levulinic acid ester, this ester is purified by distillation in the presence of a high-boiling solvent and then hydrolyzed in the presence of water and a strong acid, an aqueous levulinic acid solution being formed. This levulinic acid solution shows a slight coloration, but the levulinic acid likewise darkens rapidly under a brief thermal stress.

In spite of its disadvantages, the preparation of levulinic acid from furfuryl alcohol is the only process which has so far been carried out industrially.

In M. Conrad, Ber. Dt. Chem. Ges. 11, 211 (1878) and M. Conrad, Ann. 188, 1216 (1877), the saponification of diethyl acetylsuccinate with concentrated hydrochloric acid or with $Ba(OH)_2$ or KOH to give levulinic acid is described. In the acidic saponification, ethyl levulinate is formed as a by-product. In the alkaline saponification, elimination of the acetyl group takes place, so that succinic acid is formed as a by-product. Levulinic acid prepared in this way by saponification of diethyl acetylsuccinate shows a dark coloration even after isolation by distillation under the slightest possible temperature stress, and this rapidly deteriorates on storage.

Surprisingly, a process for the preparation of levulinic acid, starting from acetylsuccinates, has now been found, wherein color-stable levulinic acid is obtained in high purity with a good yield.

The invention therefore relates to a process for the preparation of color-stable levulinic acid by saponification of acetylsuccinates with aqueous mineral acids, which is characterized in that the starting products are continuously treated with steam in countercurrent in a reactor cascade, the reaction being carried out above the boiling point of the alcohol being formed in the reaction or above the boiling point of the aqueous azeotrope being formed.

The starting compounds used are acetylsuccinates which are derived from alcohols whose boiling point or whose boiling point in the azeotrope with water is below 100° C. Examples of such alcohols are methanol, ethanol, propanol, i-propanol, n-butanol and t-butanol. Preferably, dimethyl acetylsuccinate or diethyl acetylsuccinate and, particularly preferably, dimethyl acetylsuccinate is used. Hydrochloric acid or sulphuric acid can be used as the mineral acids, and preferably aqueous hydrochloric acid is used.

For carrying out the process, the starting compounds are mixed, the acetylsuccinate : mineral acid molar ratio being 1 : 1 to 7 : 1, preferably 3 : 1.

The starting compounds are fed to the upper part of the reactor cascade, which is preferably constructed as a tray column, and treated with steam in countercurrent, at least 0.85 kg of steam being fed per kg of acetylsuccinate.

The residence time in the reactor cascade should allow as quantitative as possible a decarboxylation of the acetylsuccinate and hydrolysis of the resulting levulinic acid esters to give levulinic acid. The residence time required for this purpose depends on the liquid level on the trays and on the number of trays. Preferably, a tray column with a defined liquid level on the trays (hold-up) is used, it being intended that the trays do not run empty. As a rule, residence times of 30–60 minutes are sufficient.

The top and bottom temperatures of the reactor cascade are controlled in such a way that the alcohol formed in the reaction is stripped out of the column together with water and $CO_2$, but the mineral acid remains in the column, a temperature difference of at least 10° C. between the top and bottom temperatures being preferably maintained. When hydrochloric acid is used as the mineral acid, a top temperature of 90°–100° C. and a bottom temperature of 110°–140° C. are preferably maintained.

Due to the continuous removal of the alcohol being formed in the hydrolysis of the levulinic acid ester resulting after the decarboxylation, the levulinic acid ester content in the end product is minimized.

At the bottom of the column, crude levulinic acid is taken off and then purified by distillation under the slightest possible temperature stress. The hydrochloric acid thus separated off can be fed back to the column if desired.

FIG. 1 shows a preferred embodiment of the process according to the invention. In FIG. 1, 1 is the reactor cascade, for example a bubble-cap tray column, 2 is the heat exchanger, 3 is a dephlegmator, 4 is the acetylsuccinate feed line, 5 is the mineral acid feed line, 6 is the feed line for the mixed starting compounds, 7 is the vapour line, 8 is the steam feed and 9 is the take-off line for crude levulinic acid.

Acetylsuccinate from line 4 is mixed with mineral acid from line 5 and the mixture is fed via line 6 to the upper part of the column at a temperature of about 100. Superheated steam is blown in via line 8 and passed upwards through the column.

In the bottom of the column, the reaction mixture running off from the lowest tray of the column is concentrated via heat exchanger 2 by evaporation of water. The crude levulinic acid formed is discharged via line 9 and purified in a downstream vacuum distillation at the slightest possible temperature stress. At the top of the column, the temperature is controlled by the dephlegmator 3 in such a way that the mineral acid is not discharged via the vapor line 7 together with the alcohol, water and $CO_2$, but predominantly remains in the crude levulinic acid. Depending on the bottom temperature, the crude levulinic acid taken off via line 9 contains differing quantities of mineral acid, which can be separated off in the vacuum distillation and fed back to the column via line 5.

By the process according to the invention, levulinic acid is obtained at short residence times in high yield and excellent color stability. As a rule, yields of 85-95% of theory, relative to acetylsuccinate, are achieved. The residence time is in general only between 30 and 60 minutes, whereby the formation of by-products, which are insoluble or cannot be separated off and which impair the purity, color and color stability, is avoided. The total reaction time is about 1-2 hours.

After purification by distillation, the levulinic acid prepared according to the invention shows a Gardener color, number of about 2 according to ASTM D1544-8, which, even under strong thermal stress, deteriorates only slowly and to a far smaller extent as compared with levulinic acid prepared by known processes.

EXAMPLE 1

In a reactor cascade, shown in FIG. 1, with 28 bubble-capped trays and a diameter of 300 mm, 87.5 kg of reaction mixture were fed per hour to tray 23. The mixture consisted of 57.5 kg of dimethyl acetylsuccinate and 30 kg of a 12% hydrochloric acid. 50 kg of steam per hour were blown into the column below the bottom tray. The bottom temperature was maintained at 115° C. 84.3 kg per hour of a vapor mixture consisting of methanol, water, $CO_2$ and a little hydrochloric acid escaped over the top. The temperature of this mixture escaping through line 5 was maintained at 99°-100° C. by means of the dephlegmator 3.

53.2 kg per hour of crude levulinic acid of the following chemical composition:
65.8% of levulinic acid
1.2% of methyl levulinate
0.2% of dimethyl acetylsuccinate
0.5% of unknown by-products (which were introduced with the technical dimethyl acetylsuccinate employed)
28.0% of water
4.3% of HCl left the bottom of the column via line 9.

The crude levulinic acid was purified by fractional vacuum distillation, 33.8 kg of pure levulinic acid being obtained per hour, corresponding to a yield of 95.2%. The levulinic acid purified in this way had a Gardener color number of 1-2 and showed no color deterioration on storage.

EXAMPLE 2

In the apparatus described in Example 1 and FIG. 1, 87.5 kg/hour of reaction mixture were fed to tray 23. The mixture consisted of 57.5 kg of dimethyl acetylsuccinate and 30 kg of the first distillate fraction from the pure levulinic acid distillation, and this was made up with 36% HCl, so that the HCl concentration was about 11-12%.

These 30 kg were composed of
57.7% of water
23.0% of levulinic acid
12.0% of HCl
6.7% of methyl levulinate
0 6% of methanol and unknown by-products.

50 kg per hour of steam were blown into the column below the bottom tray. The bottom temperature was maintained at 115° C. 71.5 kg/hour of vapor mixture consisting of methanol, water, $CO_2$ and a little hydrochloric acid escaped over the top. The temperature of this escaping mixture is maintained at 100° C. by means of the dephlegmator.

66 kg per hour of crude levulinic acid of the following chemical composition:
64.2% of levulinic acid
3.0% of methyl levulinate
0.2% of dimethyl acetylsuccinate
0.4% of unknown by-products (which are introduced with the technical dimethyl acetylsuccinate used)
28.0% of water
4.2% of HCl left the bottom of the column.

This crude levulinic acid was purified by fractional vacuum distillation, 33.5 kg per hour of pure levulinic acid being obtained, corresponding to a yield of 94.6%. The levulinic acid purified in this way had a Gardener color number of 1-2 and showed no color deterioration on storage.

COMPARISON EXAMPLE 244.6 g of dimethyl acetylsuccinate and 520 ml of HCl (17%) were heated under reflux until the end of the reaction had been reached at the end of $CO_2$ evolution. The reaction time was 5 hours. The reaction mixture was concentrated and the residue was then distilled at 0.013 bar. 86 g (57% of theory) of levulinic acid were obtained. Boiling point 138°-140° C. at 0.013 bar.

The levulinic acid thus obtained showed a Gardener color number of 2, which deteriorated to a Gardener color number of 6 after storage for one month at room temperature.

To investigate the color stability, levulinic acid prepared according to Example 1 was subjected to different thermal stresses and compared with a levulinic acid prepared (by Otsuka) from furfuryl alcohol according to DE-A 2,112,726. The results are shown in Table 1:
  a levulinic acid prepared according to Example 1
  b levulinic acid prepared (by Otsuka) from furfuryl alcohol
  c levulinic acid prepared according to the comparison example

TABLE 1

| Gardener colour number under different thermal stresses | | | | | | | | | |
|---|---|---|---|---|---|---|---|---|---|
| T(°C.) | 35 | | | 100 | | | 150 | | |
| h | a | b | c | a | b | c | a | b | c |
| 1 | 2 | 1 | 3 | 3 | 1 | 3 | 5 | 13 | 10 |
| 2 | 2 | 1 | 3 | 3 | 1 | 3 | 6 | 14 | 12 |
| 3 | 2 | 1 | 3 | 3 | 2 | 4 | 7 | 15 | 13 |
| 4 | 2 | 1 | 3 | 3 | 3 | 4 | 8 | 16 | 15 |
| 5 | 2 | 1 | 3 | 4 | 3 | 4 | 8 | 17 | 16 |
| 6 | 2 | 1 | 3 | 4 | 3 | 4 | 9 | 17 | 17 |
| 7 | 2 | 1 | 3 | 4 | 3 | 4 | 9 | 18 | 18 |
| 8 | 2 | 1 | 3 | 5 | 4 | 5 | | | |
| 9 | 2 | 1 | 3 | 5 | 4 | 6 | | | |

TABLE 1-continued

| Gardener colour number under different thermal stresses | | | | | | | | |
|---|---|---|---|---|---|---|---|---|
| T(°C.) | 35 | | | 100 | | | 150 | | |
| h | a | b | c | a | b | c | a | b | c |
| 24 | 2 | 1 | | 5 | 6 | | | | |

What is claimed is:

1. Process for the preparation of color-stable levulinic acid by saponification of an acetylsuccinate with aqueous mineral acid, comprising treating a mixture of the acetylsuccinate and mineral acid continuously with steam counter- currently in a reactor cascade, the reaction being carried out above the boiling point of the alcohol being formed in the reaction or above the boiling point of the aqueous azeotrope being formed.

2. Process according to claim 1, wherein the acetylsuccinate which is a diester of a acetylsuccinic acid which is derived from an alcohol whose boiling point or whose boiling point in the azeotrope with water is below 100° C.

3. Process according to claim 1, wherein the acetylsuccinate dimethyl acetylsuccinate is.

4. Process according to claim 1, wherein aqueous hydrochloric acid is the aqueous mineral acid.

5. Process according to claim 4, wherein the acetylsuccinate : molar ratio is 1 : 1 to 7 : 1.

6. Process according to claim 5, wherein acetylsuccinate : HCl molar ratio is 3 : 1.

7. Process according to claim 1, wherein at least 0.85 kg of steam per kg of acetylsuccinate is employed.

8. Process according to claim 1, wherein residence time in the reactor cascade is 30- 60 minutes.

9. Process according to claim 1 comprising maintaining a temperature between 110° and 140° C. in the bottom of the reactor cascade and a temperature between 90° and 100° C. at the top of the reactor cascade, a temperature difference of at least 10° C. being maintained between the top and bottom.

10. Process according to claim 1, wherein the reaction time is about 30 to 60 minutes.

11. The process according to claim 1 wherein the levulinic acid has a Gardener index of 1-2.

* * * * *